United States Patent [19]

Chen

[11] Patent Number: 5,592,193
[45] Date of Patent: Jan. 7, 1997

[54] BACKLIGHTING ARRANGEMENT FOR LCD DISPLAY PANEL

[75] Inventor: Hsing-Yao Chen, Barrington, Ill.

[73] Assignee: Chunghwa Picture Tubes, Ltd., Taipei, Taiwan

[21] Appl. No.: 529,345

[22] Filed: Sep. 18, 1995

Related U.S. Application Data

[63] Continuation of Ser. No. 209,297, Mar. 10, 1994, abandoned.

[51] Int. Cl.$^6$ .................................................. G09G 3/36
[52] U.S. Cl. ........................................... 345/102; 345/88
[58] Field of Search ............................. 345/102, 87, 88; 348/750, 751, 758; 359/48–50

[56] References Cited

U.S. PATENT DOCUMENTS

| | | | |
|---|---|---|---|
| 4,907,862 | 3/1990 | Suntola | ..................... 358/59 |
| 4,951,150 | 8/1990 | Browning . | |
| 5,089,883 | 2/1992 | Welker et al. . | |
| 5,103,328 | 4/1992 | Numao . | |
| 5,128,782 | 7/1992 | Wood . | |
| 5,135,300 | 8/1992 | Toide et al. . | |
| 5,140,449 | 8/1992 | Sluzky et al. . | |
| 5,142,388 | 8/1992 | Watanabe et al. . | |
| 5,144,471 | 9/1992 | Takanashi et al. . | |
| 5,146,354 | 9/1992 | Plesinger et al. . | |
| 5,146,355 | 9/1992 | Prince et al. . | |
| 5,162,786 | 11/1992 | Fukuda . | |
| 5,162,930 | 11/1992 | Sluzky et al. . | |
| 5,175,637 | 12/1992 | Jones et al. | .............. 359/48 |
| 5,214,521 | 5/1993 | Kwon et al. . | |
| 5,337,068 | 8/1994 | Stewart et al. | ............ 345/87 |

FOREIGN PATENT DOCUMENTS 3-198026  8/1991  Japan ....................................... 345/102

Primary Examiner—Richard Hjerpe
Assistant Examiner—Kent Chang
Attorney, Agent, or Firm—Emrich & Dithmar

[57] ABSTRACT

A video display system includes a passive display panel such as a liquid crystal display (LCD) panel including a first plurality of horizontally aligned transparent conductive scanning electrodes and a second plurality of vertically aligned transparent conductive signal electrodes disposed on opposed surfaces of the panel. Light directed onto the aft surface of the display panel is transmitted through the panel as each horizontal linear array of first scanning electrodes is turned "ON" with the horizontal linear arrays sequentially turned on for vertically scanning the display panel in a step wise manner. Time varying video image information is provided to the vertically aligned electrodes. Liquid crystal display backlighting is provided in the form of a thin, elongated light beam of uniform intensity directed onto the display panel's aft surface. The backlighting beam is vertically displaced, such as from top to bottom, in a stepwise manner over the display panel synchronously with the turning "ON" of the horizontal scanning electrodes such that the beam illuminates only the horizontal linear array of the scanning electrodes which is turned "ON" i.e., only that portion of the display panel containing visible video information, for improved video image contrast and more efficient backlighting of the display panel. The scanning back light beam is provided by a partitioned or sectioned light panel, such as a plasma discharge panel (PDP), where the partitions are each aligned with a respective horizontal array of scanning electrodes and sequentially turned "ON" synchronously with actuation of the scanning electrode arrays.

12 Claims, 3 Drawing Sheets

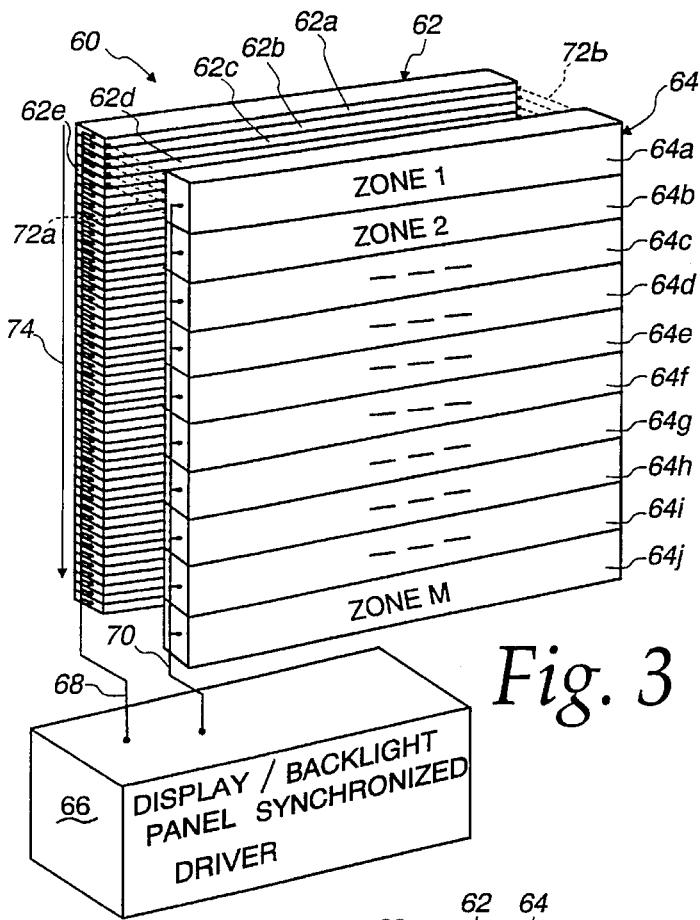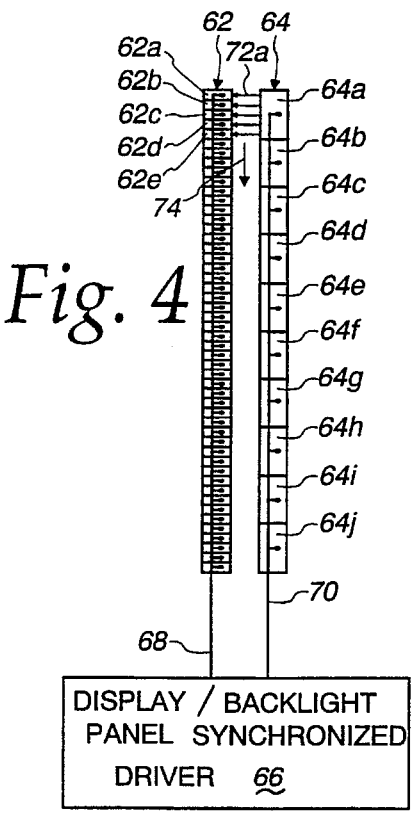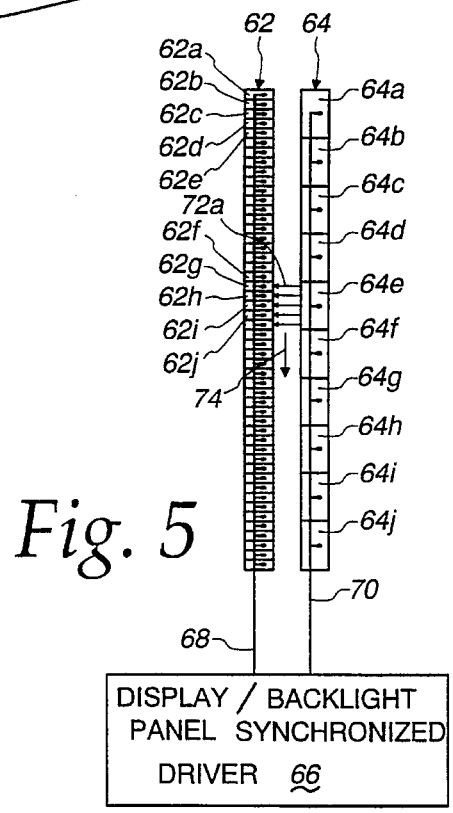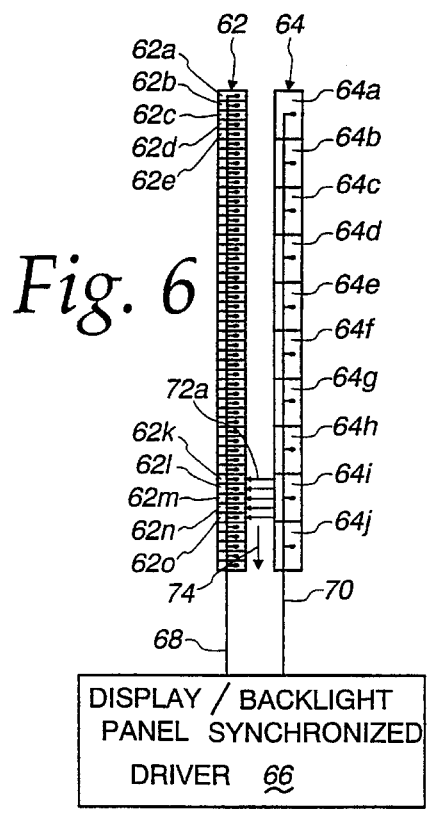

BACKLIGHTING ARRANGEMENT FOR LCD DISPLAY PANEL

This is a continuation of application Ser. No. 08/209,297, filed Mar. 10, 1994, now abandoned.

FIELD OF THE INVENTION

This invention relates generally to passive displays employing backlighting such as liquid crystal displays (LCDs) as used in television receivers and computer terminals and is particularly directed to a backlighting arrangement for an LCD display which provides improved video image contrast and more efficient display backlighting.

BACKGROUND OF THE INVENTION

A liquid crystal display (LCD) is a passive type of display for providing a video image. LCDs are commonly used in television receivers, portable computer displays, and other electronic devices. An LCD usually requires a source of back light for operation because the LCD operates effectively as a light valve, allowing transmission of light in one state and blocking transmission of light in a second state. The typical LCD panel structure includes a liquid crystal polymer encapsulated between at least two planar glass plates in parallel with each other. A polarization layer is bonded to the outer surface of each glass plate such that the glass plates are sandwiched between two polarization layers.

The inner surface, or the surface facing the liquid crystal polymer, of each glass plate includes mutually perpendicularly oriented, conductive, transparent linear arrays of electrodes. The volume of the liquid crystal polymer between any two orthogonal arrays of electrodes forms a cube whose face area constitutes a pixel. The electrode arrays are connected on the periphery of the glass plates via input/output (I/O) strips for coupling to electronic circuitry for applying a voltage to the two sets of orthogonal conductive transparent electrode arrays. To one set of linear, parallel arrays of electrodes is provided video image information (typically to the vertically aligned electrodes), while to the other linear, parallel array of electrodes (typically the array oriented horizontally) are provided "ON" signals in a sequential manner such that each horizontal linear array of electrodes is sequentially turned on rendering the portion of the liquid crystal polymer under the turned-on electrode array transparent for presenting a portion of the video image. The vertically aligned electrodes are known as "signal" electrodes, while the horizontally aligned electrodes are commonly referred to as "scanning" electrodes.

The liquid crystal polymer is disposed intermediate first and second transparent electrodes. A voltage source couples the first and second transparent electrodes via a switch. Without a proper voltage applied across the liquid crystal polymer, the liquid crystal molecules are randomly oriented and incident light is randomly scattered by the liquid crystal polymer. With the switch closed and a voltage applied across the liquid crystal polymer, the liquid crystal molecules become optically aligned with the polarizer and render the "ON" line transparent. Thus, light incident upon this line is transmitted therethrough. In a conventional LCD display, a light source is placed behind the LCD panel to illuminate the whole panel and project a video image. The light source may be a fluorescent discharge tube or a metal halide or Xenon arc lamp. At any instant during operation, the LCD panel has only one horizontal line "ON," with only this line allowing for transmission of light through the panel. Facing electrodes adjacent all other horizontal lines in the LCD panel are OFF. Therefore, most of the light from the light source aft of the panel is blocked by the non-transmitting portions of the LCD panel and converted to heat. This arrangement is characterized by low light utilization efficiency and the generation of a substantial amount of heat which must be dissipated. Also, some of the light in the non-transmitting line areas is transmitted through the LCD panel by scattering which causes loss of contrast. In a standard NTSC system with 525 horizontal scan lines in a conventional projection LCD system, it can be seen that with only 1/525th of the input light utilized for producing a useful image, much energy is wasted in a conventional projection LCD system. This waste will increase in future systems employing high definition television (HDTV) displays which employ over 1000 horizontal scan lines and which will reduce light utilization efficiency even further. In order to increase image brightness and contrast, more powerful light sources are being developed. These more powerful light sources providing more lumens with more watts of power will produce even more heat and make component cooling and heat dissipation even more important design considerations.

This invention addresses the aforementioned limitations of the prior art by providing a backlighting source for an LCD panel which brightly illuminates only that portion of the LCD panel rendered transparent and containing video information and which maintains the backlighting beam on the transparent portion as it scans the display panel.

OBJECTS AND SUMMARY OF THE INVENTION

Accordingly, it is an object of the present invention to provide improved and more efficient backlighting for a passive display panel.

It is another object of the present invention to provide backlighting for only that portion of a passive display panel which is turned "ON" for more efficient video image backlighting and minimizing of back light scattering by the display panel.

Yet another object of the present invention is to provide improved contrast and brightness in a back lighted LCD panel by illuminating only that portion of the panel upon which video information is presented.

A further object of the present invention is to reduce the heat generated in backlighting a passive display panel particularly in a projection LCD display.

A still further object is to reduce power consumption in a backlit, portable video display wherein a video image is presented in a scanned manner by illuminating only that portion of the display which provides video information at a given time for prolonging battery operation.

These objects of the present invention are achieved and the disadvantages of the prior art are avoided by a video display apparatus comprising a passive, generally planar display panel having a plurality of linear, spaced, parallel arrays of video image elements, wherein the arrays of video image elements are vertically scanned in a sequential manner from a first edge of the display panel to a second, opposed edge of the display panel in providing a plurality of spaced, parallel portions of a video image in a sequential manner on the display panel; a partitioned or sectioned planar light panel disposed generally parallel to and spaced from an aft surface of the display panel and including a plurality of linear, elongated arrays of light sources aligned generally parallel to the arrays of video image elements for directing a light beam on one or more adjacent arrays of video image elements at a given time; and synchronizing drive means coupled to the display panel and to the light panel for actuating each of the light sources in a sequential manner synchronously with the vertical scanning of the arrays of video image elements for displacing the light beam over the display panel in a scanning manner for illuminating only that portion of the display panel providing a portion of a video image at a given time.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

FIG. 3 is a simplified combined block and schematic diagram of a backlighting arrangement for an LCD display panel in accordance with the principles of the present invention;

FIGS. 4, 5, and 6 are simplified combined block and schematic diagrams of the backlighting arrangement for an LCD panel shown in FIG. 3 illustrating sequential scanning of the LCD panel by a light beam emitted by a backlighting panel in accordance with the present invention;

DETAILED DESCRIPTION OF THE PREFERRED EMBODIMENTS

Figure 1:
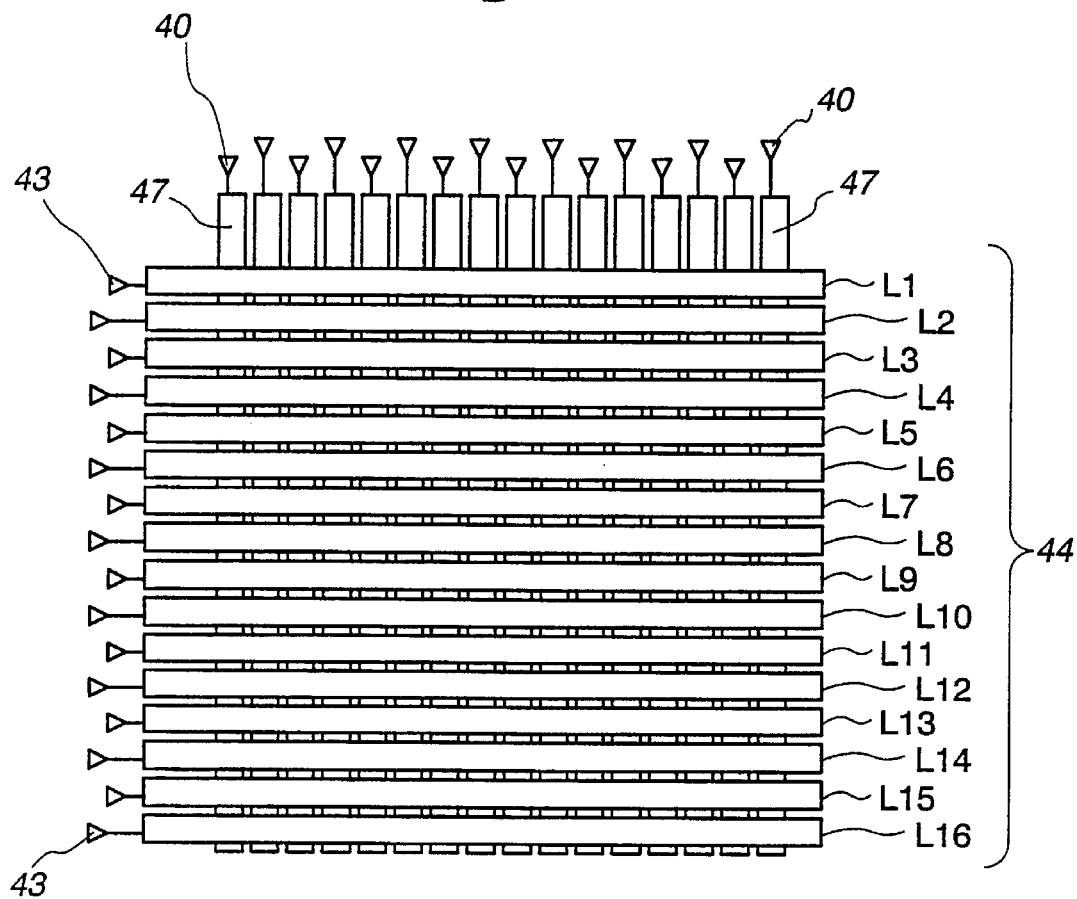
FIG. 1 is a schematic front elevation view of an LCD panel for use with the backlighting arrangement of the present invention.
Figure 2:
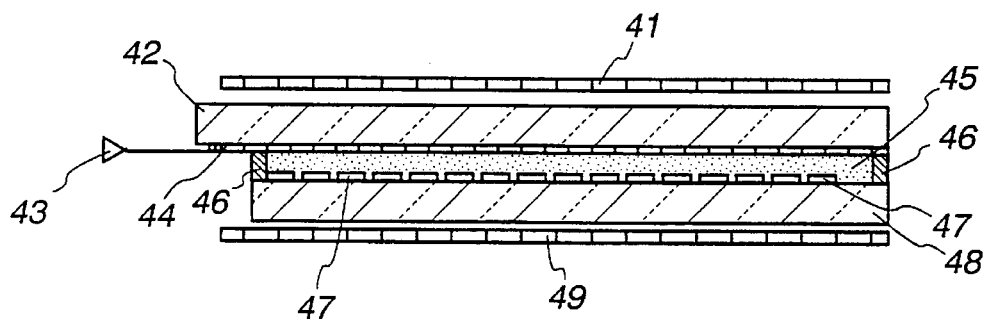
FIG. 2 is a schematic longitudinal cross-sectional view of the LCD panel shown in FIG. 1.

Referring to FIGS. 1 and 2, there are respectively shown schematic top plan and longitudinal cross-sectional views of a liquid crystal display device with which the backlighting source of the present invention is intended for use. Sixteen transparent conductive scanning electrodes 44 ($L_1$ to $L_{16}$) having a strip shape are formed in parallel with each other on the inner surface of a transparent substrate 42, and sixteen transparent conductive signal electrodes 47 for applying a video signal having a strip shape are formed in parallel with each other on the inner surface of a transparent substrate 48. A ferroelectric liquid crystal layer 45 is formed between the transparent substrates 42 and 48 and is sealed by a sealing element 46. Respective drivers 43 are connected to the respective electrodes 44 ($L_1$ to $L_{16}$) so as to apply a voltage $V_C$ thereto. Respective drivers 40 are connected to the respective signal electrodes 47 so as to apply voltages $V_S$ thereto. Polarizers 41 and 49 arranged to have a crossed Nicols relation are disposed oppositely to each other, and the backlighting source of the present invention is located adjacent the outer surface of polarizer 49, although this is not shown in the figure for simplicity. Although the liquid crystal display device is shown as having sixteen transparent conductive scanning electrodes 44, it is not limited to this arrangement of scanning and may include virtually any member of scanning electrode arrays.

Portions where the respective electrodes 44 and electrodes 47 overlap form picture elements. Voltages $V_C$ and $V_S$ are applied to corresponding electrodes 44 and 47 so as to bring a series of picture elements under one of the scanning electrodes 44 to a bright state. In this matrix type display panel, a scanning "ON" state voltage is sequentially applied to each of the scanning electrodes 44 in typically proceeding downward along the liquid crystal layer 45. As the voltage is sequentially applied to each of the scanning electrodes 44, at the same time the remaining scanning electrodes are biased to the "OFF" state, and the portion of the video image under the scanning electrode to which the "ON" state voltage is applied becomes visible on the liquid crystal layer 45. A set of time varying video image voltages are simultaneously applied to each of the vertically aligned signal electrodes 47 such that the video image presented on the liquid crystal layer 45 appears continuous.

Referring to FIG. 3, there is shown a simplified combined block and schematic diagram of an LCD display system 60 incorporating a backlighting arrangement in accordance with the present invention. FIGS. 4, 5 and 6 are simplified combined block and schematic diagrams of the backlighting arrangement for an LCD panel shown in FIG. 3 illustrating sequential scanning of the LCD panel by a light beam emitted by the backlighting panel in accordance with the present invention. The LCD display system 60 includes a planar LCD panel 62 and a planar partitioned or sectioned backlighting panel 64 arranged in a spaced manner and oriented generally parallel. LCD panel 62 includes a plurality of elongated, linear, horizontally aligned scanning electrode arrays as previously described where the upper five scanning electrode arrays are identified in the figures as elements 62a–62e. As previously described with respect to FIGS. 1 and 2, when each of the scanning electrode arrays is rendered in the "ON" state, the liquid crystal polymer under that particular electrode array becomes transparent to light directed onto an aft surface of the LCD panel 62 for providing a portion of a video image thereon. Each of the scanning electrode arrays is rendered in the "ON" state in a sequential manner in proceeding downwardly along the LCD panel 62 in the direction of arrow 74.

The partitioned backlighting panel 64 includes a plurality of elongated, generally linear, horizontally aligned light-emitting zones 64a–64j. Each of the light emitting zones 64a–64j is aligned generally parallel with the scanning electrode arrays of the LCD panel 62. As shown in FIG. 3, the partitioned backlighting panel 64 includes light-emitting zone 1 identified as element 64a through light emitting zone M identified as element 64j.

A display/backlight panel synchronized driver 66 is coupled to LCD panel 62 by means of a first line, or lead, 68. More specifically, the display/backlight panel synchronized driver 66 is electrically coupled to each of the scanning electrode arrays within LCD panel 62 for sequentially actuating each of the scanning electrode arrays in the direction of arrow 74 in providing video image information in a sequential manner on LCD panel. The display/backlight panel synchronized driver 66 is further coupled to the partitioned backlighting panel 64 by means of a second line 70. More specifically, the display/backlight panel synchronized driver 66 is coupled to each of the backlighting panel's light emitting zones 64a–64j. The display/backlight panel synchronized driver 64 actuates each of the light-emitting zones 64a–64j in a sequential manner downwardly in the direction of arrow 74. This downward "ON" sequencing of the light-emitting zones 64a–64j is performed synchronously with the sequential actuation of the LCD panel's scanning electrode arrays.

The sequential actuation of the LCD panel's scanning electrode arrays and the partitioned backlighting panel's light emitting zones 64a–64j is shown in FIGS. 4–6. In these figures, a light beam emitted by one of the light emitting zones is shown as a series of vertically spaced rays, or arrows, 72a. As shown in FIG. 4, the uppermost light emitting zone 64a initially directs light beam 72a on the uppermost scanning electrode arrays 62a–62e of the LCD panel 62. With the electrode arrays and light emitting zones sequentially scanned downwardly in the direction of arrow 74, an intermediate light emitting zone 64e projects light beam 72a onto the aft surfaces of a plurality of adjacent scanning electrode arrays 62f–62j located in a center portion of the LCD panel 62 as shown in FIG. 5. As the scanning of the electrode arrays and light emitting zones continues downwardly, a light emitting zone 64i, located near the bottom of the partitioned backlighting panel 64 directs the light beam 72a on the aft surfaces of a plurality of adjacent scanning electrode arrays 62k–62o located near the bottom of the LCD panel 62. Following actuation of the lowermost scanning electrode arrays in LCD panel 62 and turn-on of the bottom light emitting zone 64j of the partitioned backlighting panel 64, retrace is initiated on the LCD panel and partitioned backlighting panel to allow for another downward scanning of the LCD panel and partitioned backlighting panel for presenting the next frame of a video image.

As shown in the figures, the light beam 72 emitted by each of the light emitting zones 64a–64j covers a plurality of adjacent, vertically-spaced scanning electrode arrays. The present invention is not limited to this arrangement, but will operate equally as well with the light beam 72a having the same or even a smaller vertical dimension than the scanning electrode arrays.

With the arrangement shown in the figures where the light beam 72a has a greater vertical dimension than the scanning electrode arrays of the LCD panel 62, the scanning electrode arrays may be actuated in either an interlaced or a non-interlaced manner as the LCD panel 62 is scanned downwardly. In both cases, only 1/N of the surface area of the partitioned backlighting panel emits light at a given time which significantly reduces the power requirements of this LCD panel backlighting arrangement. Due to the reduced power requirements, the inventive backlighting arrangement is particularly adapted for use in portable battery-powered display systems such as laptop personal computers. Reduced output power of the backlighting source also reduces heat dissipation requirements in the display and results in a corresponding increase in system reliability.

Figure 7:
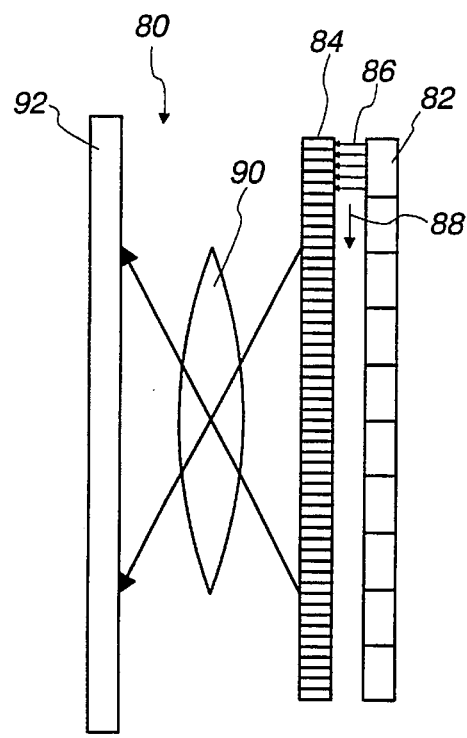
FIG. 7 is a simplified combined block and schematic diagram of a backlighting arrangement for an LCD panel in a projection display system in accordance with another embodiment of the present invention.

Referring to FIG. 7, there is shown a simplified schematic diagram of a projection display system 80 incorporating the display panel backlighting arrangement of the present invention. The projection display system 80 includes a partitioned backlighting panel 82 for directing a light beam 86 on an aft surface of an LCD panel 84. As in the previously described embodiment, the partitioned backlighting panel 82 includes a plurality of light emitting zones, while LCD panel 84 includes a plurality of scanning electrode arrays. The light emitting zones and scanning electrode arrays are aligned generally parallel and allow for vertical scanning of light beam 86 downwardly in the direction of arrow 88 synchronously with downward scanning of the parallel electrode arrays in LCD panel 84. With light beam 86 directed through each portion of LCD panel 84 sequentially rendered transparent, a video image is projected from the forward surface of the LCD panel onto a focusing lens 90 and thence onto a projection screen 92 for viewing.

Although disclosed primarily in terms of an LCD display panel, the present invention is not limited to use with this type of display panel. Rather, the backlighting arrangement of the present invention may be employed with virtually any type of passive display panel. Similarly, the partitioned backlighting panel may be comprised of any of the more conventional backlighting arrangements. For example, the partitioned backlighting panel may be comprised of a plurality of aligned flourescent tubes, plasma discharge panels (PDPs), electroluminescent panels or gaseous discharge lamps.

Figure 8:
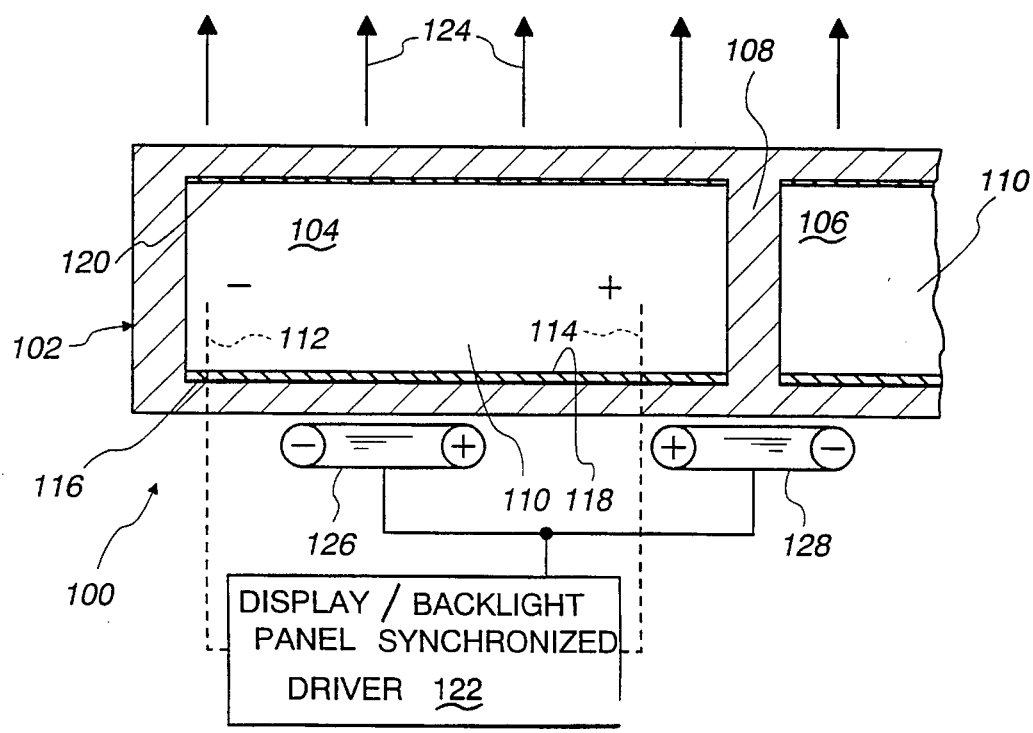
FIG. 8 is a simplified combined block and schematic diagram of a portion of a plasma discharge panel for use in one embodiment of the LCD backlighting arrangement of the present invention.

Referring to FIG. 8, there is shown a simplified sectional view of a portion of a plasma discharge panel (PDP) 100 for use in one embodiment of the backlighting arrangement of the present invention. PDP 100 includes a generally rectangular panel housing 102 having a plurality of spaced, elongated chambers each extending the length of the panel and arranged in a partitioned manner. Thus, housing 102 includes first and second chambers 104 and 106 separated by a partition 108. Disposed within the first and second chambers is a fill gas 110. Disposed on an aft surface of each of the chambers, as shown in the figure for the case of the first chamber 104, are a reflective material layer 116 and a nonmetallic rear plate 118. The nonmetallic rear plate 118 is comprised of a light emitting material such as phosphor. Similarly, a phosphor layer 120 is disposed on a forward, inner surface of each of the chambers.

Disposed adjacent an aft surface of housing 112 are a plurality of RF coils 126 and 128. Each of the RF coils 126, 128 is coupled to and energized by a display/backlight panel synchronized driver 122. When energized by the display/backlight panel synchronized driver 122, the RF coils 126 and 128 produce a rapidly changing magnetic field which induces an electric field within each of the chambers 104 and 106 for ionizing the fill gas 110 therein. Ionization of the fill gas 110 causes a plasma arc discharge within chambers 104 and 106 whereby ultraviolet radiation from the arc discharge excites the non-metallic rear plate (phosphor) 118 and phosphor layer 120 disposed on facing inner walls of each of the chambers. With a forward portion of the housing 112 transparent, visible light is emitted in the direction of arrows 124 onto an aft surface of a passive display panel which is not shown in the figure for simplicity. The display/backlight panel synchronized driver 122 is also coupled to a passive display panel (not shown) as previously described for sequentially actuating its scanning electrode arrays in providing a video image. By timed sequencing of the actuation of each of the RF coils 126 and 128, a light beam may be emitted from housing 102 in the direction of arrows 124 and sequentially scanned over the housing between adjacent gas filled chambers for illuminating adjacent portions of the passive display panel.

An alternative embodiment of discharge panel 100 is shown in dotted line form as including first and second electrodes 112 and 114 within the first chamber 104. The first and second electrodes 112, 114 are coupled to and energized by the display/backlight panel synchronized driver 122 for causing an electrical discharge of the fill gas 110 within the first chamber resulting in visible light being emitted in the direction of arrows 124 from a forward surface of housing 102. Thus, backlighting for a passive display panel can be provided by the sequential electrical discharge within adjacent light beam emitting chambers in a display backlighting panel.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

I claim:

1. A video display apparatus comprising:
   a passive, generally planar color liquid crystal display panel having a plurality of linear, spaced, parallel arrays of video image elements, wherein said arrays of video image elements are vertically scanned in a sequential manner from a first edge of said display panel to a second, opposed edge of said display panel in providing a plurality of spaced, parallel portions of a video image in a sequential manner on said display panel, and wherein a complete scan of said video image elements defines a picture field;
   a partitioned planar light panel disposed generally parallel to and spaced from an aft surface of said display panel and including a plurality of linear, elongated arrays of light sources aligned generally parallel to said arrays of video image elements for directing a white light beam on one or more adjacent arrays of video image elements at a given time; and
   synchronizing drive means coupled to said display panel and to said light panel for actuating each of said light sources in a sequential manner synchronously with the vertical scanning of said arrays of video image elements for displacing said white light beam over said display panel in a scanning manner for illuminating only that portion of said display panel providing a portion of a video image at a given time, wherein all of said light sources are sequentially scanned within a picture field;
   wherein said arrays of video image elements are greater in number than said arrays of light sources, and wherein each array of light sources directs a white light beam onto a plurality of adjacent, spaced arrays of video image elements, and wherein said arrays of video image elements are scanned in a continuous manner at a first constant scan rate and said arrays of light sources are scanned in a continuous manner at a second constant scan rate, and wherein said first scan rate is greater than said second scan rate, and wherein reduced light energy is used by directing a white light beam from a single array of light sources at a given time onto a plurality of video image elements in said display panel.

2. The video display apparatus of claim 1 wherein said light panel is a plasma discharge panel.

3. The video display apparatus of claim 1 wherein said light panel is a vaccuum flourescent panel.

4. The video display apparatus of claim 1 wherein said display panel is a gas discharge panel.

5. The video display apparatus of claim 1 wherein the first edge of said display panel is at an upper portion thereof and the second edge of said display panel is at a lower portion thereof, and wherein said light beam scans said display panel from top to bottom.

6. The video display apparatus of claim 1 further comprising a projection screen disposed adjacent to and aligned with said display panel for displaying a video image on said projection screen.

7. The video display apparatus of claim 1 wherein said light panel is an electroluminescent panel.

8. A display apparatus for providing a video image comprising:
   a passive, generally planar color liquid crystal display panel having a plurality of horizontally aligned, vertically spaced, elongated, generally linear arrays of video image elements, wherein said arrays of video image elements are sequentially scanned in a vertical direction from a first edge of said panel to a second, opposed edge of said panel to provide in a timed manner a plurality of vertically spaced, horizontally aligned portions of a video image, and wherein a full image is formed during a complete scan of said video image elements from said first edge to said second edge of said panel, and wherein a complete scan of said video image elements defines a picture field;
   a partitioned planar light panel disposed in a parallel, spaced manner from an aft surface of said display panel, wherein said light panel includes a plurality of horizontally aligned, vertically spaced, elongated, generally linear arrays of white light emitting zones, and wherein each of said white light emitting zones directs an elongated, narrow white light beam on an adjacent array of video image elements in said display panel; and
   drive means coupled to each of said arrays of video image elements and each of said arrays of white light emitting zones for actuating said arrays of video image elements and said arrays of white light emitting zones in a sequential, timed manner, wherein all of said white light emitting zones are sequentially scanned within a picture field and wherein a plurality of adjacent arrays of video image elements and a single array of white light emitting zones are actuated at a given time, and wherein said adjacent arrays of video image elements and said single array of white light emitting zones actuated at a given time are disposed adjacent one another and are in mutual horizontal alignment such that only that portion of said display panel defined by adjacent linear arrays of video image elements providing a portion of a video image is illuminated by a white light beam at a given time;
   wherein said arrays of video image elements are greater in number than said arrays of white light emitting zones, and wherein each array of white light emitting zones directs a white light beam onto a plurality of adjacent, spaced arrays of video image elements, and wherein said arrays of video image elements are scanned in a continuous manner at a first constant scan rate and said arrays of light emitting zones are scanned in a continuous manner at a second constant scan rate with said first scan rate greater than said second scan rate, and wherein reduced light energy is used by directing a white light beam from a single array of light sources at a given time onto a plurality of adjacent, spaced arrays of video image elements in said display panel.

9. The apparatus of claim 8 wherein said display panel is a liquid crystal display panel.

10. The apparatus of claim 8 further comprising projection means disposed adjacent a forward surface of said liquid crystal display panel for providing a projection video display.

11. The apparatus of claim 8 wherein said arrays of video image elements are scanned downwardly from a first upper edge to a second lower edge of said display panel.

12. The apparatus of claim 8 wherein said light panel is a plasma discharge panel, a vacuum fluorescent panel, a gas discharge panel, or an electroluminescent panel.

* * * * *